United States Patent
Kalayeh

(10) Patent No.: US 7,333,184 B2
(45) Date of Patent: Feb. 19, 2008

(54) GROUND SURFACE COVER TYPE REFLECTIVITY VARIATION CORRECTION IN A DIFFERENTIAL ABSORPTION LIDAR SYSTEM

(75) Inventor: Hooshmand Mahmood Kalayeh, Pittsford, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 277 days.

(21) Appl. No.: 11/174,019

(22) Filed: Jul. 1, 2005

(65) Prior Publication Data

US 2007/0002306 A1    Jan. 4, 2007

(51) Int. Cl.
*G01C 3/08* (2006.01)
*G01N 21/00* (2006.01)

(52) U.S. Cl. .................. 356/4.07; 356/337; 356/342

(58) Field of Classification Search ........... 356/4.01, 356/4.07, 337, 342, 432–444; 250/338.1, 250/338.5, 339.1, 339.11; 73/335.01
See application file for complete search history.

(56) References Cited

U.S. PATENT DOCUMENTS 4,450,356 A * 5/1984 Murray et al. ......... 250/339.11
6,822,742 B1 * 11/2004 Kalayeh et al. .......... 356/437
6,864,983 B2 * 3/2005 Galle et al. .............. 356/437
2004/0263852 A1 * 12/2004 Degtiarev et al. ......... 356/437

FOREIGN PATENT DOCUMENTS

EP        489546 A2 *  6/1992

* cited by examiner

*Primary Examiner*—Isam Alsomiri
(74) *Attorney, Agent, or Firm*—RatnerPrestia

(57) ABSTRACT

A method for improving the accuracy of estimating concentration path length of a target molecule using a differential absorption LIDAR (DIAL) system. In particular, this method allows improved detection of plumes containing the target molecule against inhomogeneous background, such as uncovered ground or ground with various types of cover. In an embodiment of the present invention, spectral surface reflectivity variations are systematically corrected based on interpolation of surface reflectivity measurements of multiple offline beams of different wavelengths, which are relatively close to the online wavelength. In another embodiment, the signal to noise ratio of the received online pulse energy is improved by using multiple laser beams having the online wavelength and the signal to noise ratio of the received pulse energies at an offline wavelength is improved by using multiple laser beams having that offline wavelength.

19 Claims, 3 Drawing Sheets

GROUND SURFACE COVER TYPE REFLECTIVITY VARIATION CORRECTION IN A DIFFERENTIAL ABSORPTION LIDAR SYSTEM

FIELD OF THE INVENTION

The present invention relates to a method for improving the accuracy of estimating concentration path length of a target molecule using a differential absorption LIDAR (DIAL) system. In particular, this method allows improved detection of plumes containing the target molecule against inhomogeneous background, such as ground with various types of cover.

BACKGROUND OF THE INVENTION

In a DIAL system, the received back scattered signal is a function of: the transmitted laser pulse energy; the speed of light; the laser pulse width; the telescope area (field of view); the range (inverse square law); the offline beam and online beam overlap and the field of view (i.e. the geometric form factor); the spectral response of the receiver optics; the plume transmission; the total atmospheric transmission; and the ground cover type.

One use of a two-line DIAL system is to estimate the concentration path length (CPL) of a fluid related plume. Therefore, the online wavelength is desirably selected such that it is only absorbed by the target molecule of the fluid and nothing else in the optical path. The offline wavelength is desirably selected such that it is not absorbed by the target molecule. More desirably, the online and offline wavelengths are selected such that the ratio of the geometric form factor, the spectral response of the receiver optics, and the surface reflectivity corresponding to the online and offline wavelengths are approximately the same. As may be seen in Equation 1, when this condition is met, these parameters may cancel out, simplifying calculation of the CPL.

$$CPL = \frac{\ln\left(\frac{E(\lambda_{Off}, R)E_1(\lambda_{On})\xi(R_{On})\xi(\lambda_{On})\rho(\lambda_{On})}{E(\lambda_{On}, R)E_1(\lambda_{Off})\xi(R_{Off})\xi(\lambda_{Off})\rho(\lambda_{Off})}\right) - 2\int_0^R (k(\lambda_{On}, r) - k(\lambda_{Off}, r))dr}{2(\sigma(\lambda_{On}) - \sigma(\lambda_{Off}))} - RC_{t-bag},$$

(Eq. 1)

where $\lambda_{On/Off}$ is the online (or offline) peak wavelength, $\sigma(\lambda_{On/Off})$ is the online (or offline) cross-section, $E_1(\lambda_{On/Off})$ is the online (or offline) transmitted laser pulse energy, R is the range/altitude/distance of the sensor to the target, $E(\lambda_{On/Off}, R)$ is the online (or offline) received laser pulse energy, $\xi(R_{On/Off})$ is the geometric form factor for the online (or offline) peak wavelength, $\xi(\lambda_{On/Off})$ is the spectral response of the receiver optics for the online (or offline) peak wavelength, $\rho(\lambda_{On/Off})$ is the background surface reflectance for the online (or offline) peak wavelength, $k(\lambda_{On/Off}, r)$ is the atmospheric attenuation coefficient for the online (or offline) peak wavelength, and $C_{t-bag}$ is the target molecule concentration in the atmosphere.

In practice, however, when the geometric form factor, the spectral response of the receiver optics, and the surface reflectivity corresponding to the online and offline wavelengths are not approximately the same, then the values of these parameters for each online and offline measurement must be measured to accurately estimate the target plume CPL. The geometric form factor and spectral response of the receiver optics corresponding to the online and offline wavelengths may be measured and the DIAL system may be calibrated accordingly. Unfortunately, correcting for reflectivity variations due to ground surface cover type may be difficult in many situations. If these ground surface cover type reflectivity variations are not properly corrected, significant errors in CPL estimates of the target molecule may result, leading to false identification of plumes (or lack of plumes).

The present invention relates to an improved method of correcting for ground surface cover type reflectivity variations in DIAL measurements. Improved methods of the present invention may increase the probability of detection of plumes containing the target molecule. For example, these improved methods may be useful in identification of plumes generated by leaks in pipelines or storage tanks, plumes caused by spills and other contamination, and naturally occurring plumes such as gases emitted by volcanoes.

SUMMARY OF THE INVENTION

An exemplary embodiment of the present invention is a method for determining concentration path length of a target molecule. At least three pulsed laser beams are transmitted substantially collinearly through a region of interest onto a surface. These pulsed laser beams include: an online laser beam having an online peak wavelength within an optical absorption band of the target molecule; and a number of offline laser beams. Each offline laser beam has one of a corresponding set of offline peak wavelengths, each of which is outside of the optical absorption band of the target molecule. The transmitted pulse energy of each of the pulsed laser beams is measured. The pulsed laser beams are reflected from the surface and back through the region of interest to be incident on an array of optical sensors, which measure a received pulse energy of the portion of each of the pulsed laser beams that is incident on the array. A scaled received pulse energy of each of the offline laser beams is determined using the transmitted pulse energy and the received pulse energy of the portion of each of the offline laser beams. The reflectivity ratio of the online peak wavelength to one of the offline peak wavelengths for the surface is estimated based on the scaled received pulse energies of the offline laser beams, the online peak wavelength, and the offline peak wavelengths. The concentration path length for the target molecule is calculated using the transmitted pulse energy and the received pulse energy of the online laser beam, the estimated reflectivity ratio, and the transmitted pulse energy and the received pulse energy of the offline laser beam corresponding to the offline peak wavelength used to estimate the reflectivity ratio.

Another exemplary embodiment of the present invention is a method for determining concentration path length of a target molecule. At least three pulsed laser beams are transmitted substantially collinearly through a region of interest onto a surface. These pulsed laser beams include: an online laser beam having an online peak wavelength within an optical absorption band of the target molecule; and a number of offline laser beams. Each offline laser beam has one of a corresponding set of offline peak wavelengths, each of which is outside of the optical absorption band of the target molecule. The transmitted pulse energy of each of the pulsed laser beams is measured. The pulsed laser beams are reflected from the surface and back through the region of interest to be incident on an array of optical sensors, which measure a received pulse energy of the portion of each of the pulsed laser beams that is incident on the array. A scaled received pulse energy of each of the offline laser beams is determined using the transmitted pulse energy and the received pulse energy of the portion of each of the offline laser beams. The scaled zero concentration path length received pulse energy of the online laser beam is estimated based on the scaled received pulse energies of the offline laser beams, the online peak wavelength, and the set of offline peak wavelengths. The concentration path length for the target molecule is calculated using the transmitted pulse energy and the received pulse energy of the online laser beam and the scaled zero concentration path length received pulse energy of the online laser beam.

An addition exemplary embodiment of the present invention is a method for determining concentration path length of a target molecule. At least four pulsed laser beams are transmitted substantially collinearly through a region of interest onto a surface. These pulsed laser beams include: a number of pulsed online laser beams having an online peak wavelength that is within an optical absorption band of the target molecule; and a number of pulsed offline laser beams having an offline peak wavelength that is outside of the optical absorption band of the target molecule. An average transmitted online pulse energy of the online laser beams is determined, as is an average transmitted offline pulse energy of the offline laser beams. Each of the pulsed laser beams is reflected from the surface and back through the region of interest to be incident on an array of optical sensors. An average received online pulse energy and an average received offline pulse energy of portions of the pulsed laser beams that are incident on the array of optical sensors are determined. The concentration path length for the target molecule is calculated using the average transmitted online pulse energy, the average transmitted offline pulse energy, the received online pulse energy, and the received offline pulse energy.

A further exemplary embodiment of the present invention is a differential absorption LIDAR (DIAL) system. The DIAL system includes: an online pulsed laser source to generate an online laser beam; a number of offline pulsed laser sources, each adapted to generate an offline laser beam; a first array of optical sensors optically coupled to the online laser beam and the plurality of offline laser beams to sense transmitted pulse energies of each of the laser beams; optics to align the online laser beam and the plurality of offline laser beams such that the laser beams are transmitted substantially collinearly through a region of interest to reflect from a surface; a second array of optical sensors arranged to receive reflected portions of each of the laser beams and sense received pulse energies of the reflected portion of each laser beam; and a DIAL data processor electrically coupled to the first array of optical sensors and the second array of optical sensors. The online laser beam has an online peak wavelength within an optical absorption band of a target molecule and each offline pulsed laser beam has one of a corresponding set of offline peak wavelengths. Each of the set of offline peak wavelengths is outside of the optical absorption band of the target molecule. The DIAL data processor includes: a determination module; an estimation module; and a calculation module. The determination module determines a scaled received pulse energy of each of the offline laser beams using the transmitted pulse energies of the offline laser beams sensed by the first array of optical sensors and the received pulse energies of the reflected portions of the offline laser beams sensed by the second array of optical sensors. The estimation module estimates at least one of: the reflectivity ratio of the online peak wavelength to one of the set of offline peak wavelengths for the surface based on the scaled received pulse energy of the offline laser beams, the online peak wavelength, and the set of offline peak wavelengths; or the scaled zero concentration path length received pulse energy of the online laser beam based on the scaled received pulse energy of the offline laser beams, the online peak wavelength, and the set of offline peak wavelengths. The calculation module calculates the concentration path length for the target molecule using the transmitted pulse energy of the online laser beam sensed by the first array of optical sensors, the received pulse energy of the online laser beam sensed by the second array of optical sensors, and at least one of: the estimated reflectivity ratio and the scaled received pulse energy of the offline laser beam corresponding to the one of the set of offline peak wavelengths; or the estimated scaled zero concentration path length received pulse energy of the online laser beam.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawing are the following figures.

DETAILED DESCRIPTION OF THE INVENTION

Figure 1:
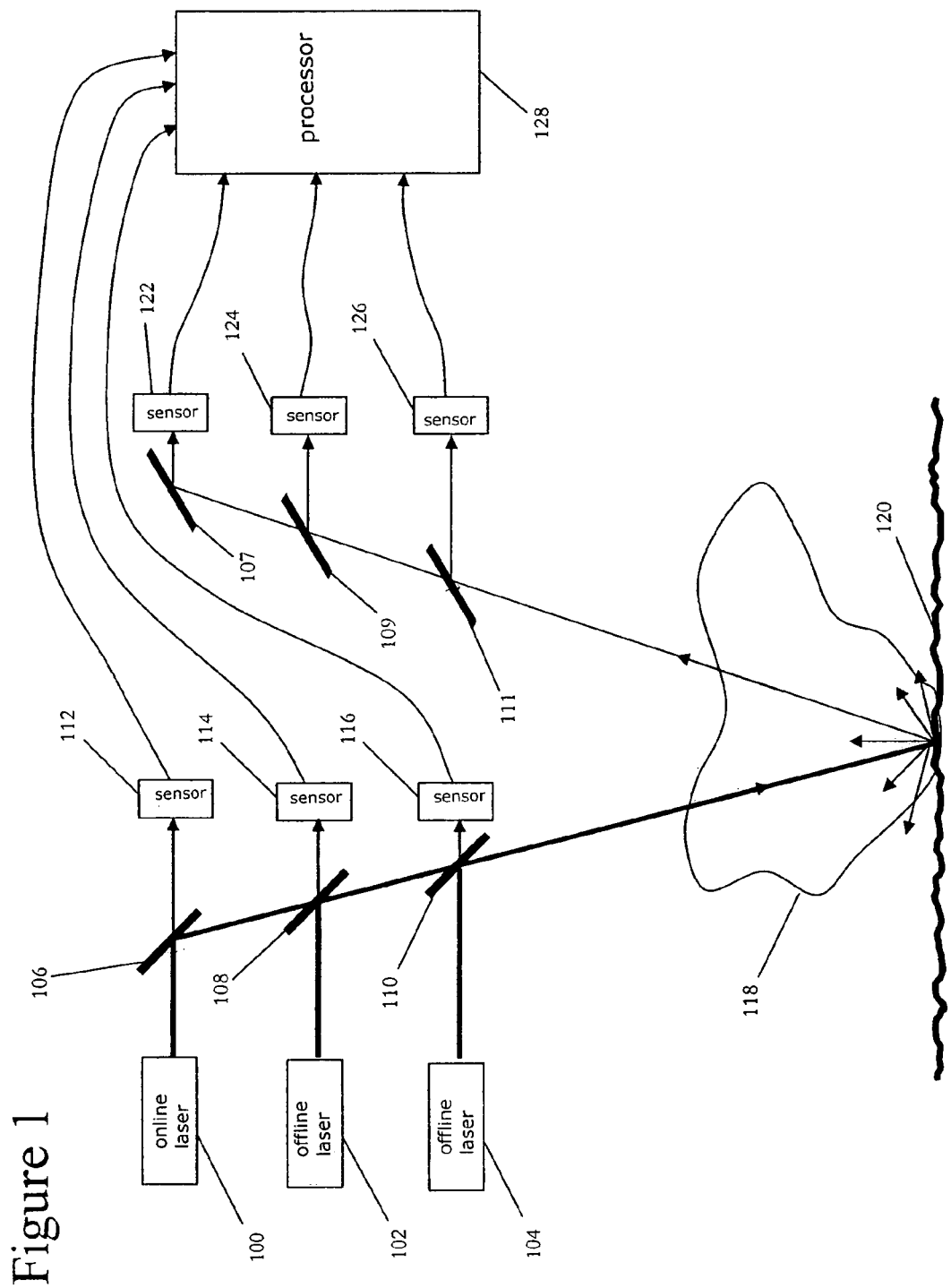
FIG. 1 is a schematic block diagram illustrating an exemplary differential absorption LIDAR (DIAL) system according to the present invention.

An exemplary embodiment of the present invention is a differential absorption LIDAR (DIAL) system, as illustrated in FIG. 1. This exemplary system includes three pulsed laser sources, online pulsed laser source 100 and two offline pulsed laser sources 102 and 104. It is noted that the selection of two offline pulsed laser sources in the exemplary embodiment of FIG. 1 is not intended to be limiting. The discussion of exemplary DIAL systems below primarily focuses on the exemplary embodiment of FIG. 1, but it is contemplated that one skilled in the art would understand that additional offline pulsed laser sources may be included in an exemplary DIAL system according to the present invention.

Online pulsed laser source 100 generates an online laser beam that includes a series of laser pulses. These pulses of the online laser beam have an online peak wavelength, $\lambda_{On}$, that is within an optical absorption band of the target molecule. The online peak wavelength is desirably outside of the optical absorption bands of other atmospheric molecules that may be in the region of interest as well to minimize interference from absorption of the online laser beam by these non-target molecules.

Thus, the concentration path length of the target molecule within a region of interest may be determined using the resulting attenuation of the pulse energy of the online laser beam as the laser pulses propagate through the region of interest. Pulsed laser sources are desirably used to reduce problems of potential signal fluctuation due to environmental effects, such as wind, that may vary the location and density of a plume containing the target molecule during a long exposure measurement. Such variations may lead to confusing results for DIAL systems using continuous wave sources.

The transmitted pulse energy of the online laser beam, $E_1(\lambda_{On})$, may desirably be determined from a small portion of each pulse directed to optical sensor 112. This optical sensor forms part of an array of optical sensors that also includes optical sensors 114 and 116 which may be used to detect the transmitted pulse energies of the online and offline laser beams. The small portion of the online laser beam detected by optical sensor 112 may be separated using beam splitter 106, as shown in FIG. 1.

Each offline pulsed laser source 102 and 104 generates an offline laser beam of laser pulses having one of a corresponding set of offline peak wavelengths, $\{\lambda_{Off1}, \lambda_{Off2}\}$. These offline peak wavelengths are selected to be outside of the optical absorption band of the target molecule so that the pulse energy of the offline laser pulse is not significantly affected by existence, or non-existence, of the target molecule along the beam path of the offline laser beams through the region of interest. The offline peak wavelengths are also desirably outside of the optical absorption bands of other atmospheric molecules that may be in the region of interest. This selection of the offline peak wavelengths may minimize interference from absorption of the offline laser beams by these non-target molecules.

As with the online laser beam, the transmitted pulse energies of the offline laser beams, $E_1(\lambda_{Off1,2})$, may desirably be determined from a small portion of each pulse directed to optical sensors 114 and 116, respectively. The small portion of the first offline laser beam may be separated using first dichroic beam splitter 108, which desirably reflects substantially all light with a wavelength $\lambda_{Off1}$ and transmits substantially all light with a wavelength $\lambda_{On}$. Similarly, the small portion of the second offline laser beam may be separated using second dichroic beam splitter 110, which desirably reflects substantially all light with a wavelength $\lambda_{Off2}$ and transmits substantially all light with wavelengths of $\lambda_{Off1}$ or $\lambda_{On}$, as shown in FIG. 1.

The array of optical sensors 112, 114, and 116 are coupled to provide signals proportional to the transmitted pulse energies of the three laser beams to DIAL data processor 128 for use in calculating the concentration path length (CPL) of the target molecule.

Beam splitter 106 and dichroic mirrors 108 and 110 may also operate as transmission optics to align the online laser beam and the offline laser beams such that the laser beams may be transmitted substantially collinearly through the region of interest. In this way, the online laser beam and each of the offline laser beams may sample approximately the same beam path through the region of interest. Such similar beam paths are desirable to reduce any differences in the conditions experienced by the laser beams, other than those caused by the different wavelengths of the three laser beams, e.g. absorption of online laser beam by target molecules in plume 118. Also, the similarity of the beam paths is desirable so that the three laser beams may all be reflected from substantially the same area of inhomogeneous surface 120.

Although the exemplary embodiment of FIG. 1 is shown with beam splitter 106 and dichroic mirrors 108 and 110 act both to separate the portions of each beam to be monitored by the array of optical sensors 112, 114, and 116 and to align the three laser beams substantially collinearly, it is contemplated that additional optical components, such as mirrors, gratings, and lens, may be included as well to accomplish these tasks. It is noted that it may also be desirable for the three laser beams to be substantially collimated to reduce spreading of the beams along the beam path from the exemplary DIAL system to inhomogeneous surface 120 and back. Other alternative exemplary optics to separate the portions of each beam for monitoring and to align the three laser beams substantially collinearly are described in U.S. Pat. No. 6,822,742 to Kalayeh, which is incorporated herein by reference.

In many practical applications, inhomogeneous surface 120 may be a section of ground, which may have a variety of different forms of cover arranged over it, e.g. shrubs, trees, grass, pavement, etc. As shown in FIG. 1, inhomogeneous surface 120 and the various cover on it may appear rough. Thus, much of the pulse energy of each of the laser beams may be scattered and only a small amount of each pulse may make it back to the DIAL system to be measured.

The reduced optical signal caused by reflecting (scattering) the laser beams from a rough surface may adversely affect sensitivity of CPL detection by reducing the signal to noise ratio of the exemplary DIAL system. Further, the variations in ground cover may lead to differences in the reflectivity of inhomogeneous surface 120 from one measurement position to another.

The exemplary embodiment of FIG. 1 includes a second set of optics, dichroic mirrors 109 and 111 and mirror 107, to collect, separate by peak wavelength, and direct the reflected portions of the two offline laser beams and the online laser beam received by the exemplary DIAL system to a second array of optical sensors 122, 124, and 126. Desirably, dichroic mirrors 109 and 111 may have properties similar to dichroic mirrors 108 and 110, respectively. It is noted that this second set of receiver optics may include additional optical elements (not shown) as described above for the set of transmission optics.

The second array of optical sensors 122, 124, and 126 sense the received pulse energies of the reflected portion of the online laser beam, $E(\lambda_{On}, R)$, the first offline laser beam, $E(\lambda_{Off1}, R)$, and the second offline laser beam, $E(\lambda_{Off2}, R)$, respectively. This array of optical sensors is coupled to DIAL data processor 128 to provide signals proportional to the transmitted pulse energies of the three laser beams to DIAL data processor 128 for use in calculating the concentration path length (CPL) of the target molecule.

DIAL data processor 128 uses the transmitted offline pulse energy signals from optical sensors 114 and 116 and the received offline pulse energy signals from optical sensors 124 and 126 to determine a scaled received pulse energy of each of the offline laser beams, $E_{Off1,2}$. Desirably the received pulse energy value of each offline laser beam may be scaled to units of the corresponding transmitted pulse energy. These scaled received offline pulse energy values may be calibrated using known transmission coefficients of dichroic mirrors 108, 109, 110, and 111, as well as known conversion factors for optical sensors 114, 116, 124, and 126.

Using the scaled received pulse energy of the offline laser beams, the online peak wavelength of the online laser beam, and the set of offline peak wavelengths of the offline laser beam, DIAL data processor 128 then estimates at least one of: a reflectivity ratio of the online peak wavelength to one of the set of offline peak wavelengths for the area of the inhomogeneous surface, $$\frac{\rho(\lambda_{On})}{\rho(\lambda_{Off1})};$$

and/or a scaled zero concentration path length received pulse energy of the online laser beam, $E_{0-CPL}$.

The scaled received pulse energy of each offline laser beam is proportional to the reflectivity of the corresponding offline peak wavelength for the reflecting area of the inhomogeneous surface. Assuming that other factors, such as the geometric form factor and the spectral response of the receiver optics for the offline peak wavelengths are substantially equal (or known and taken into account during determination of scaled received offline pulse energies), the proportionality factor for the scaled received pulse energy of each offline laser beam to the reflectivity of the corresponding offline peak wavelength for the reflecting area of the inhomogeneous surface may be equal. Therefore, the scaled received pulse energies of the offline laser beams may be used to provide a graph of the relative reflectivity as a function of wavelength for the area of the surface from which beams are reflecting. Interpolating between points of this graph and the online peak wavelength may provide an improved estimate of the reflectivity ratio of the online peak wavelength to one of the set of offline peak wavelengths for the area of the inhomogeneous surface.

The DIAL data processor may then calculate the CPL for the target molecule using the transmitted pulse energy of the online laser beam, the received pulse energy of the online laser beam, the estimated reflectivity ratio, and the scaled received pulse energy of the offline laser beam for which the reflectivity ratio was estimated. This calculation may be performed using Equation 1.

Alternatively, the DIAL data processor may estimate the scaled zero CPL received pulse energy of the online laser beam, $E_{0-CPL}$. Because the offline peak wavelengths are selected to be outside of the optical absorption band of the target molecule, the offline laser beams desirably have a zero CPL for the target molecule. Therefore, if the scaled received pulse energies of the offline laser beams are graphed as a function of wavelength the resulting curve may represent zero CPL scaled received pulse energies as a function of wavelength. Interpolating between points of this graph and the online peak wavelength may provide an improved estimate of the scaled zero CPL received pulse energy of the online laser beam.

The CPL for the target molecule may then be using the transmitted pulse energy of the online laser beam, the received pulse energy of the online laser beam, and the estimated scaled zero CPL received pulse energy of the online laser beam. This calculation may be performed using Equation 1 and replacing the offline received pulse energy with the estimated scaled zero CPL received pulse energy, the offline cross-section with zero, and the remaining offline data with the corresponding online data.

DIAL data processor may include one or more of: special purpose circuitry; an application specific integrated circuit (ASIC); or a general purpose computer programmed to process the DIAL data. Each of these potential elements may be used to perform at least one of the determining, estimating and calculating functions of the DIAL data processor.

Figure 2:
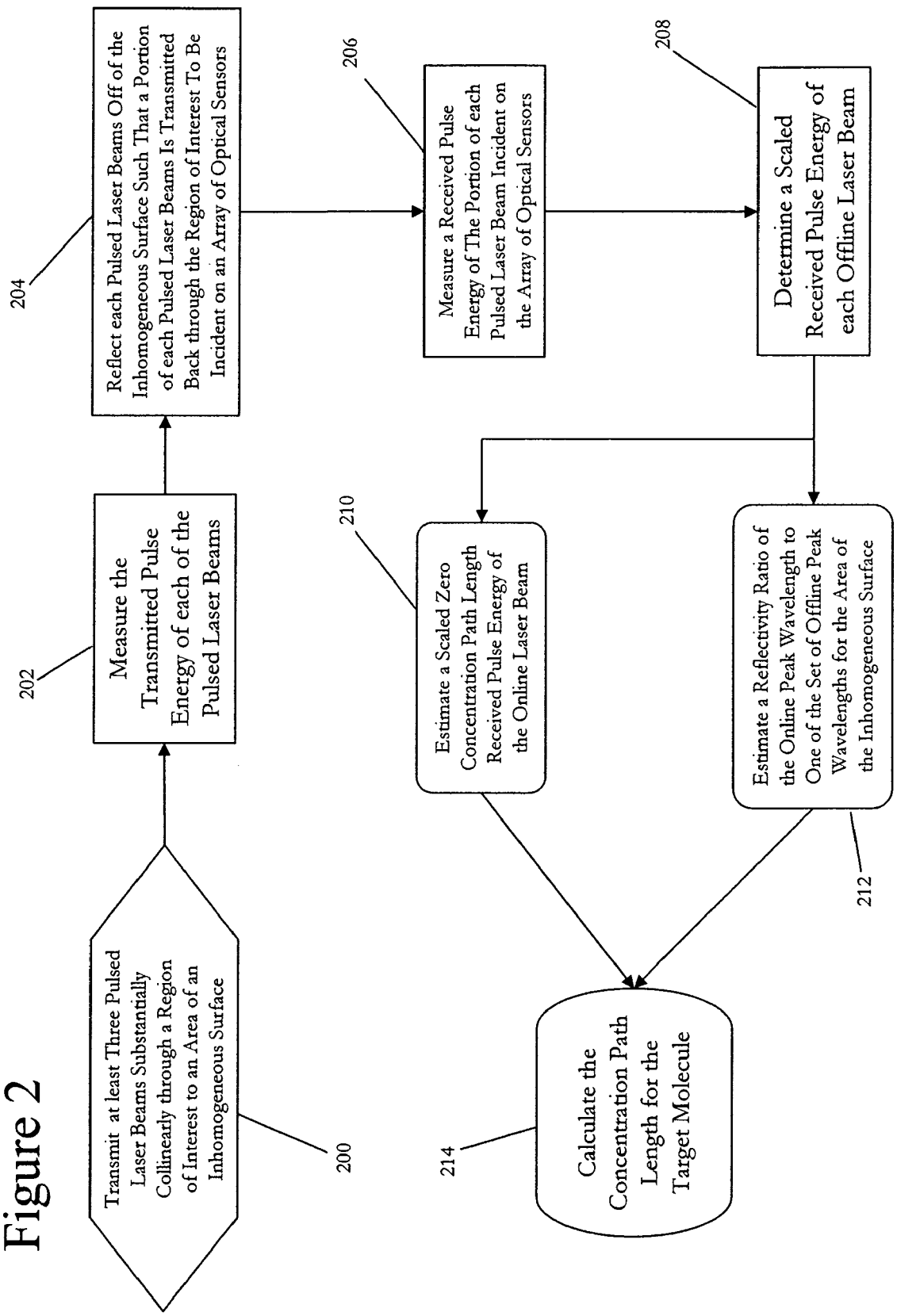
FIG. 2 is a flow chart illustrating two alternative exemplary methods of determining concentration path length for a target molecule, according to the present invention.

FIG. 2 illustrates two alternative exemplary methods for determining a concentration path length for a target molecule. At least three pulsed laser beams are transmitted substantially collinearly through a region of interest and are incident upon an area of an inhomogeneous surface, step 200. An online laser beam and at least two offline laser beams make up the at least three laser beams. The online laser beam has an online peak wavelength within an optical absorption band of the target molecule, while each of the offline laser beams has one of a corresponding set of offline peak wavelengths, which are outside of the optical absorption band of the target molecule. It is noted that it may be desirable for the offline peak wavelengths to include at least one wavelength longer and at least one wavelength shorter than the online peak wavelength. If the number of offline peak wavelengths is even, it may be desirable to have equal numbers of offline peak wavelengths longer and shorter than the online peak wavelength. It may further be desirable for the offline peak wavelengths, and possibly the online wavelength, to be equal spaced in wavelength to simplify the interpolation algorithm(s) to be used.

The transmitted pulse energy of each of the pulsed laser beams is measured, step 202. These pulse energies may be desirably measured by splitting off a small portion of each laser beam and coupling each portion into an optical sensor.

Each of the pulsed laser beams is reflected from the area of the inhomogeneous surface, step 204. The inhomogeneous surface has a reflectivity that is unknown for the online peak wavelength, and may be unknown at each of the offline peak wavelengths as well. As noted above with respect to FIG. 1, this inhomogeneous surface may include covered ground and/or open ground. The covered ground may have a variety of different forms of cover arranged over it. Thus, the reflectivity of the inhomogeneous surface at the online peak wavelength may vary with position and/or wavelength. Therefore, it may be desirable for the offline peak wavelengths to be not too far outside of the optical absorption band of the target molecule so that any variations in the reflectivity of the surface between the offline peak wavelengths and the online peak wavelength may be small, or at least smooth. For example, if two offline laser beams are used, the absolute difference between each of the offline peak wavelengths and the online peak wavelength may desirably be less than twice the width of the optical absorption band of the target molecule that includes the online peak wavelength.

It is also noted that this reflecting step in the present invention may include substantial scattering of each of the laser beams from the area of the inhomogeneous surface. However, whether or not reflection of the laser beams from the area of the inhomogeneous surface includes significant scattering, the reflection is such that a portion of each pulsed laser beam is transmitted back through the region of interest and is incident on an array of optical sensors. Each optical sensor of the array is desirably adapted to detect one of the pulsed laser beams.

The received pulse energy of the portion of each of the pulsed laser beams that is incident on the array of optical sensors is measured, step 206. The measured amount of pulse energy may be very small, e.g. 100 pJ or less, particularly when there is significant scattering of the laser beams by the inhomogeneous surface. Therefore, the optical sensors in the array may desirably be highly sensitive narrow bandwidth optical detectors.

A scaled received pulse energy of each of the offline laser beams is determined, step 208. As described above, with reference to FIG. 1, a DIAL data processor uses the transmitted offline pulse energies measured in step 202 and the received offline pulse energies measured in step 206 to determine a scaled received pulse energy of each of the offline laser beams, $\{E_{Offx}\}$, where x ranges from 1 to the number of offline laser beams. Desirably the received pulse energy value of each offline laser beam may be scaled to units of the corresponding transmitted pulse energy. These scaled received offline pulse energy values may be calibrated using known parameters of the exemplary DIAL system.

Following the determination of the scaled received pulse energies of the offline laser beams in step 208, the exemplary method of FIG. 2 may use the scaled received pulse energy of the offline laser beams in one or both of the alternative estimation steps, step 210 and step 212.

Alternative step 210, involves estimating a scaled zero concentration path length received pulse energy of the online laser beam, $E_{0\text{-}CPL}$. This estimation is based on the scaled received pulse energy of the offline laser beams determined in step 208, the online peak wavelength, and the set of offline peak wavelengths. As described above, with reference to FIG. 1, $E_{0\text{-}CPL}$ may be estimated using a linear interpolation algorithm. Because the offline peak wavelengths are selected to be outside of the optical absorption band of the target molecule, the offline laser beams desirably have a zero CPL for the target molecule. Therefore, if the scaled received pulse energies of the offline laser beams are graphed as a function of wavelength the resulting curve may represent zero CPL scaled received pulse energies as a function of wavelength. Interpolating between points of this graph and the online peak wavelength may provide an improved estimate of $E_{0\text{-}CPL}$.

One skilled in the art may understand that this interpolation may also be performed analytically. For example, if the are only two offline laser beams, i.e. a first offline laser beam and a second offline laser beam, then the linear interpolation algorithm for estimating $E_{0\text{-}CPL}$ involves calculating the result of Equation 2.

$$E_{0\text{-}CPL} = \frac{E_{Off2}(\lambda_{On} - \lambda_{Off1}) + E_{Off1}(\lambda_{Off2} - \lambda_{On})}{(\lambda_{Off2} - \lambda_{Off1})}, \quad \text{(Eq. 2)}$$

where $\lambda_{On}$ is the online peak wavelength, $\lambda_{Offx}$ is the first or second offline peak wavelength (x=1 or 2), and $E_{Offx}$ is the scaled received pulse energy of the first or second offline laser beam.

If more than two offline laser beams are used, any standard interpolation algorithm, such as a chi-squared linear interpolation algorithm or a smooth curve interpolation algorithm, may be used to estimate $E_{0\text{-}CPL}$. If a polynomial fitting algorithm is used as a smooth curve interpolation algorithm to estimate $E_{0\text{-}CPL}$, it may be desirable to use a polynomial fitting algorithm of an order equal to one less than the number of offline laser beams to reduce the chances of a degenerate solution. Alternatively, lower order polynomial fitting algorithm, such as a chi-squared quadratic fitting algorithm may be used.

Once $E_{0\text{-}CPL}$ is estimated, the CPL for the target molecule may be calculated, step 214, using the transmitted pulse energy of the online laser beam, $E_1(\lambda_{On})$, measured in step 202, the received pulse energy of the online laser beam, $E(\lambda_{On},R)$, measured in step 206, and the estimated scaled zero CPL received pulse energy of the online laser beam, $E_{0\text{-}CPL}$, estimated in step 210. This calculation may be performed using Equation 1 and replacing the offline received pulse energy $E(\lambda_{Off},R)$ with $E_{0\text{-}CPL}$, the offline cross-section, $\sigma(\lambda_{Off})$, with zero, and the remaining offline data with the corresponding online data. After canceling, these replacements lead to Equation 3.

$$CPL = \frac{\ln\left(\frac{E_{0\text{-}CPL}}{E(\lambda_{On}, R)}\right)}{2\sigma(\lambda_{On})} - RC_{t\text{-}bag}. \quad \text{(Eq. 3)}$$

Alternatively, following the determination of the scaled received pulse energies of the offline laser beams in step 208, the reflectivity ratio of the online peak wavelength to one of the set of offline peak wavelengths for the area of the inhomogeneous surface, $$\frac{\rho(\lambda_{On})}{\rho(\lambda_{Off1})},$$

may be estimated, step 212. This estimation may desirably be based on the scaled received pulse energy of each offline laser beam, the online peak wavelength, and the set of offline peak wavelengths. As described above, with reference to FIG. 1, $$\frac{\rho(\lambda_{On})}{\rho(\lambda_{Off1})}$$

may be estimated using a linear interpolation algorithm.

The scaled received pulse energy of each offline laser beam is proportional to the reflectivity of the corresponding offline peak wavelength for the reflecting area of the inhomogeneous surface. Assuming that other factors, such as the geometric form factor and the spectral response of the receiver optics for the offline peak wavelengths are substantially equal (or known and taken into account during determination of scaled received offline pulse energies), the proportionality factor for the scaled received pulse energy of each offline laser beam to the reflectivity of the corresponding offline peak wavelength for the reflecting area of the inhomogeneous surface may be equal.

Therefore, the scaled received pulse energies of the offline laser beams may be used to provide a graph of the relative reflectivity as a function of wavelength for the area of the surface from which beams are reflecting. Interpolating between points of this graph and the online peak wavelength may provide an improved estimate of the reflectivity ratio of the online peak wavelength to one of the set of offline peak wavelengths for the area of the inhomogeneous surface.

One skilled in the art may understand that this interpolation may also be performed analytically. For example, if the are only two offline laser beams, i.e. a first offline laser beam and a second offline laser beam, then the linear interpolation algorithm for estimating $$\frac{\rho(\lambda_{On})}{\rho(\lambda_{Off1})}$$

involves calculating the result of Equation 4.

$$\frac{\rho(\lambda_{On})}{\rho(\lambda_{Off1})} = \frac{\frac{E_{Off2}}{E_{Off1}}(\lambda_{On} - \lambda_{Off1}) + (\lambda_{Off2} - \lambda_{On})}{(\lambda_{Off2} - \lambda_{Off1})}, \quad \text{(Eq. 4)}$$

where $\lambda_{On}$ is the online peak wavelength, $\lambda_{Offx}$ is the first or second offline peak wavelength (x=1 or 2), and $E_{Offx}$ is the scaled received pulse energy of the first or second offline laser beam.

If more than two offline laser beams are used, any standard interpolation algorithm, such as a chi-squared linear interpolation algorithm or a smooth curve interpolation algorithm, may be used to estimate $$\frac{\rho(\lambda_{On})}{\rho(\lambda_{Off1})}.$$

If a polynomial fitting algorithm is used as a smooth curve interpolation algorithm to estimate $$\frac{\rho(\lambda_{On})}{\rho(\lambda_{Off1})},$$

it may be desirable to use a polynomial fitting algorithm of an order equal to one less than the number of offline laser beams to reduce the chances of a degenerate solution. Alternatively, lower order polynomial fitting algorithm, such as a chi-squared quadratic fitting algorithm may be used.
Once $$\frac{\rho(\lambda_{On})}{\rho(\lambda_{Off1})}$$

is estimated, the CPL for the target molecule may be calculated, step 214, using the transmitted pulse energy of the online laser beam, $E_1(\lambda_{On})$, measured in step 202, the received pulse energy of the online laser beam, $E(\lambda_{On},R)$, measured in step 206, the reflectivity ratio, $$\frac{\rho(\lambda_{On})}{\rho(\lambda_{Off1})}$$

estimated in step 212, and the data corresponding to the offline laser beam having an offline peak wavelength of $\lambda_{Off1}$. Thus, Equation 1 may be rewritten as Equation 5 and used in this calculation.

$$CPL = \quad \text{(Eq. 5)}$$
$$\frac{\ln\left(\frac{E(\lambda_{Off1}, R)E_1(\lambda_{On})\xi(R_{On})\xi(\lambda_{On})\rho(\lambda_{On})}{E(\lambda_{On}, R)E_1(\lambda_{Off1})\xi(R_{Off1})\xi(\lambda_{Off1})\rho(\lambda_{Off1})}\right) - 2\int_0^R (k(\lambda_{On}, r) - k(\lambda_{Off1}, r))dr}{2(\sigma(\lambda_{On}) - \sigma(\lambda_{Off1}))} - RC_{t-bag}.$$

Figure 3:
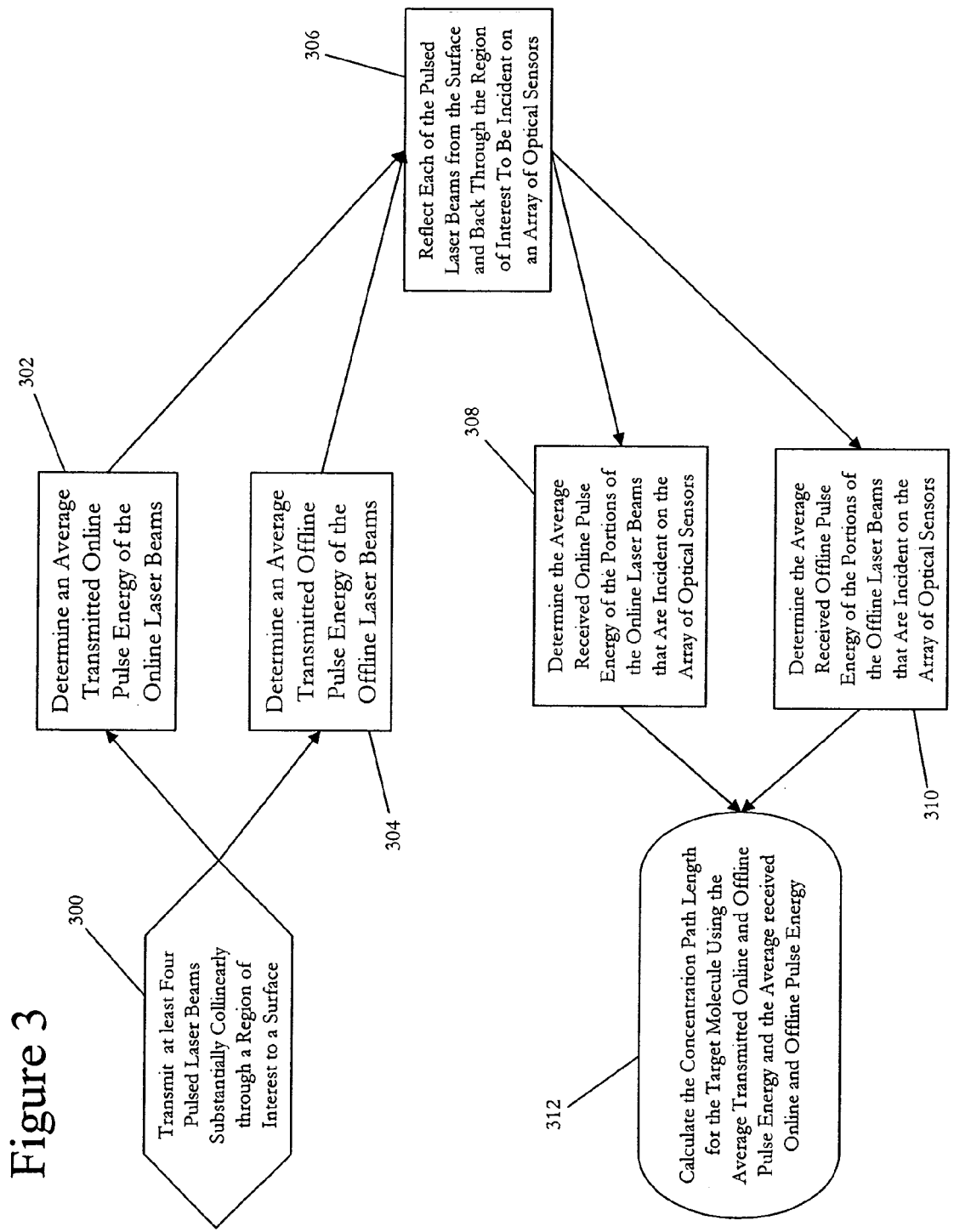
FIG. 3 is a flow chart illustrating another exemplary method of improving signal to noise ratio in a DIAL system for determining concentration path length for a target molecule, according to the present invention.

FIG. 3 illustrates an addition exemplary embodiment of the present invention is a method for determining concentration path length of a target molecule. At least four pulsed laser beams are transmitted substantially collinearly through a region of interest onto a surface, step 300. These pulsed laser beams include: at least two pulsed online laser beams that have an online peak wavelength within an optical absorption band of the target molecule; and at least two pulsed offline laser beams having an offline peak wavelength that is outside of the optical absorption band of the target molecule.

An average transmitted online pulse energy of the online laser beams is determined, step 302, as is an average transmitted offline pulse energy of the offline laser beams, step 304. These average transmitted pulse energies may be determined by measuring the pulse energies of each of the laser beams separately and then separately averaging the pulse energies of the online laser beams and the offline laser beams. Alternatively, a portion of the combined laser beams may be incident on a pair of optical sensors, the first of this pair of optical sensors being sensitive to the online peak wavelength and not the offline peak wavelength and the second optical sensor being sensitive to the offline peak wavelength and not the online peak wavelength. The average transmitted online pulse energy is proportional to the pulse energy measured by the first detector and the average transmitted offline pulse energy is proportional to the pulse energy measured by the second detector.

Each of the pulsed laser beams is reflected from the surface and back through the region of interest to be incident on an array of optical sensors, step 306. The average received online pulse energy of portions of the online pulsed laser beams that are incident on the array of optical sensors are determined, step 308, and the average received offline pulse energy of portions of the offline pulsed laser beams that are incident on the array of optical sensors are determined, step 310. These average received pulse energies may be determined using the exemplary methods described above for determining the average transmitted pulse energies. As noted above with reference to FIG. 2, the amount of received pulse energy may be very small. By combining the received pulse energies from a number of laser beams, the signal level of the received laser beams may be increased. This may also increase the signal to noise ratio of the received pulse energy measurements. It is noted that averaging the pulse energies similarly increases the signal to noise ratio by reducing the noise level. Although the present method is described in terms of averaging the pulse energies, one skilled in the art would understand that the pulse energies may be combined instead without departing from the present invention.

The concentration path length for the target molecule is calculated, step 312, using the average transmitted online pulse energy, the average transmitted offline pulse energy, the received online pulse energy, and the received offline pulse energy. These averaged parameters may be substituted for the parameters in Equation 1. Additionally, another set of offline laser beams having a different offline peak wavelength may be transmitted as well and average parameters determined for it as well. The average parameters may then be using in either of the alternative exemplary methods of FIG. 2.

The present invention includes exemplary methods to improve the calculation of the concentration path length of a target molecule. These exemplary methods allows increased accuracy in estimating the reflectivity of inhomogeneous surfaces used top reflect laser beams in exemplary DIAL systems. Such techniques may be useful in a number of technologies, such as remote sensing of chemical leaks and contamination. Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method for determining concentration path length of a target molecule, the method comprising the steps of:
   a) transmitting at least three pulsed laser beams substantially collinearly through a region of interest onto a surface, the at least three pulsed laser beams including:
      an online laser beam having an online peak wavelength within an optical absorption band of the target molecule; and
      a plurality of offline laser beams, each of the plurality of offline laser beams having one of a corresponding set of offline peak wavelengths, each of the set of offline peak wavelengths being outside of the optical absorption band of the target molecule;
   b) measuring a transmitted pulse energy of each of the at least three pulsed laser beams;
   c) reflecting each of the at least three pulsed laser beams from the surface and back through the region of interest to be incident on an array of optical sensors;
   d) measuring a received pulse energy of a portion of each of the at least three pulsed laser beams that is incident on the array of optical sensors;
   e) determining a scaled received pulse energy of each of the plurality of offline laser beams using the transmitted pulse energy of each of the plurality of offline laser beams measured in step (b) and the received pulse energy of the portion of each of the plurality of offline laser beams measured in step (d);
   f) estimating a reflectivity ratio of the online peak wavelength to one of the set of offline peak wavelengths for the surface based on the scaled received pulse energy of each of the plurality of offline laser beams, the online peak wavelength, and the set of offline peak wavelengths; and
   g) calculating the concentration path length for the target molecule using the transmitted pulse energy of the online laser beam measured in step (b), the received pulse energy of the online laser beam measured in step (d), the reflectivity ratio estimated in step (f), the transmitted pulse energy of the offline laser beam corresponding to the one of the set of offline peak wavelengths measured in step (b), and the received pulse energy of the offline laser beam corresponding to the one of the set of offline peak wavelengths measured in step (d);
   wherein the plurality of offline laser beams includes first and second offline laser beams having first and second offline peak wavelengths, respectively; and
   step (f) includes estimating the reflectivity ratio, using linear interpolation among (i) the first offline peak wavelength, (ii) the online peak wavelength and (iii) the second offline peak wavelength.

2. The method according to claim 1, wherein step (f) includes estimating the reflectivity ratio of the online wavelength to one of the set of offline wavelengths for the surface using a linear interpolation algorithm.

3. The method according to claim 2, wherein:
the plurality of offline laser beams consists of a first offline laser beam and a second offline laser beam; and
the set of offline peak wavelengths consists of a first offline peak wavelength of the first offline laser beam and a second offline peak wavelength of the second offline laser beam.

4. The method according to claim 3, wherein:
the first offline peak wavelength of the first offline laser beam is shorter than the online peak wavelength; and
the second offline peak wavelength of the second offline laser beam is longer than the online peak wavelength.

5. The method according to claim 4, wherein:
an absolute difference between the first offline peak wavelength and the online peak wavelength is less than twice a width of the optical absorption band of the target molecule that includes the online peak wavelength; and
an absolute difference between the second offline peak wavelength and the online peak wavelength is less than twice the width of the optical absorption band of the target molecule that includes the online peak wavelength.

6. The method according to claim 4, wherein:
the first offline peak wavelength and the second offline peak wavelength are approximately equidistant from the online peak wavelength.

7. The method according to claim 3, wherein:
the linear interpolation algorithm includes calculating;

$$\frac{\rho(\lambda_{On})}{\rho(\lambda_{Off1})} = \frac{\frac{E_{Off2}}{E_{Off1}}(\lambda_{On} - \lambda_{Off1}) + (\lambda_{Off2} - \lambda_{On})}{(\lambda_{Off2} - \lambda_{Off1})};$$

where $\lambda_{On}$ is the online peak wavelength, $\lambda_{Offx}$ is the first or second offline peak wavelength (x=1 or 2), $$\frac{\rho(\lambda_{On})}{\rho(\lambda_{Off1})}$$

is is the reflectivity ratio of the online peak wavelength to the first offline peak wavelength for the surface, and is the scaled received pulse energy of the first or second offline laser beam.

8. The method according to claim 2, wherein:
the plurality of offline laser beams includes at least three offline laser beams; and
the linear interpolation algorithm includes a chi-squared line fitting algorithm.

9. The method according to claim 1, wherein:
the plurality of offline laser beams consists of N offline laser beams, where N is an integer greater than two; and
step (f) includes estimating the reflectivity ratio of the online wavelength to one of the set of offline wavelengths for the surface using a smooth curve interpolation algorithm.

10. The method according to claim 9, wherein the smooth curve interpolation algorithm is a polynomial fitting algorithm of order N−1.

11. The method according to claim 9, wherein the smooth curve interpolation algorithm includes a chi-squared quadratic fitting algorithm.

12. The method according to claim 9, wherein:
N is an even integer greater than 2;
N/2 of the offline peak wavelengths are shorter than the online peak wavelength; and N/2 of the offline peak wavelengths are longer than the online peak wavelength.

13. The method according to claim 9, wherein the N offline peak wavelengths and the online peak wavelength are substantially equally spaced in wavelength.

14. The method according to claim 1, wherein reflecting each of the at least three pulsed laser beams from the surface in step (c) includes substantial scattering of each of the at least three pulsed laser beams from the area.

15. The method according to claim 1, wherein the surface includes at least one of covered ground or open ground.

16. A differential absorption LIDAR (DIAL) system, comprising:
   an online pulsed laser source to generate an online laser beam having an online peak wavelength within an optical absorption band of a target molecule;
   a plurality of offline pulsed laser sources, each offline pulsed laser source adapted to generate an offline laser beam having one of a corresponding set of offline peak wavelengths, each of the set of offline peak wavelengths being outside of the optical absorption band of the target molecule;
   a first array of optical sensors optically coupled to the online laser beam and the plurality of offline laser beams to sense transmitted pulse energies of each of the laser beams;
   optics to align the online laser beam and the plurality of offline laser beams such that the laser beams are transmitted substantially collinearly through a region of interest to reflect from a surface;
   a second array of optical sensors arranged to receive reflected portions of each of the online laser beam and the plurality of offline laser beams and sense received pulse energies of the reflected portion of each laser beam; and
   a DIAL data processor electrically coupled to the first array of optical sensors and the second array of optical sensors, the DIAL data processor including:
      a determination module to determine a scaled received pulse energy of each of the plurality of offline laser beams using the transmitted pulse energy of each of the plurality of offline laser beams sensed by the first array of optical sensors and the received pulse energy of the reflected portion of each of the plurality of offline laser beams sensed by the second array of optical sensors;
      an estimation module to estimate
      a reflectivity ratio of the online peak wavelength to the set of offline peak wavelengths for the surface based on the scaled received pulse energy of each of the plurality of offline laser beams, the online peak wavelength, and the set of offline peak wavelengths; and
      a calculation module to calculate concentration path length for the target molecule using the transmitted pulse energy of the online laser beam sensed by the first array of optical sensors, the received pulse energy of the online laser beam sensed by the second array of optical sensors, and
      the estimated reflectivity ratio and the scaled received pulse energy of the offline laser beam corresponding to the set of offline peak wavelengths;
   wherein the set of offline peak wavelengths includes first and second offline peak wavelengths, respectively; and
   estimating the reflectivity ratio includes using linear interpolation among (i) the first offline peak wavelength, (ii) the online peak wavelength and (iii) the second offline peak wavelength.

17. The DIAL system according to claim 16, wherein the DIAL data processor includes at least one of:
   special purpose circuitry;
   an ASIC; or
   a general purpose computer programmed to perform at least one of the determining, estimating and calculating functions of the DIAL data processor.

18. A method for determining concentration path length of a target molecule, the method comprising the steps of:
   a) transmitting at least three pulsed laser beams substantially collinearly through a region of interest onto a surface, the at least three pulsed laser beams including:
      an online laser beam having an online peak wavelength within an optical absorption band of the target molecule; and
      a plurality of offline laser beams, each of the plurality of offline laser beams having one of a corresponding set of offline peak wavelengths, each of the set of offline peak wavelengths being outside of the optical absorption band of the target molecule;
   b) measuring a transmitted pulse energy of each of the at least three pulsed laser beams;
   c) reflecting each of the at least three pulsed laser beams from the surface and back through the region of interest to be incident on an array of optical sensors;
   d) measuring a received pulse energy of a portion of each of the at least three pulsed laser beams that is incident on the array of optical sensors;
   e) determining a scaled received pulse energy of each of the plurality of offline laser beams using the transmitted pulse energy of each of the plurality of offline laser beams measured in step (b) and the received pulse energy of the portion of each of the plurality of offline laser beams measured in step (d);
   f) estimating a reflectivity ratio of the online peak wavelength to one of the set of offline peak wavelengths for the surface based on the scaled received pulse energy of each of the plurality of offline laser beams, the online peak wavelength, and the set of offline peak wavelengths; and
   g) calculating the concentration path length for the target molecule using the transmitted pulse energy of the online laser beam measured in step (b), the received pulse energy of the online laser beam measured in step (d), the reflectivity ratio estimated in step (f), the transmitted pulse energy of the offline laser beam corresponding to the one of the set of offline peak wavelengths measured in step (b), and the received pulse energy of the offline laser beam corresponding to the one of the set of offline peak wavelengths measured in step (d);
   wherein step (f) includes estimating the reflectivity ratio of the online wavelength to one of the set of offline wavelengths for the surface using a linear interpolation algorithm;
   the plurality of offline laser beams consists of a first offline laser beam and a second offline laser beam;
   the set of offline peak wavelengths consists of a first offline peak wavelength of the first offline laser beam and a second offline peak wavelength of the second offline laser beam;
   the first offline peak wavelength of the first offline laser beam is shorter than the online peak wavelength;
   the second offline peak wavelength of the second offline laser beam is longer than the online peak wavelength;
   an absolute difference between the first offline peak wavelength and the online peak wavelength is less than twice a width of the optical absorption band of the target molecule that includes the online peak wavelength; and an absolute difference between the second offline peak wavelength and the online peak wavelength is less than twice the width of the optical absorption band of the target molecule that includes the online peak wavelength.

19. The method according to claim 18, wherein:

the linear interpolation algorithm includes calculating;

$$\frac{\rho(\lambda_{On})}{\rho(\lambda_{Off1})} = \frac{\frac{E_{Off2}}{E_{Off1}}(\lambda_{On} - \lambda_{Off1}) + (\lambda_{Off2} - \lambda_{On})}{(\lambda_{Off2} - \lambda_{Off1})};$$

where $\lambda_{On}$ is the online peak wavelength, $\lambda_{Offx}$ is the first or second offline peak wavelength (x=1 or 2), $$\frac{\rho(\lambda_{On})}{\rho(\lambda_{Off1})}$$

is the reflectivity ratio of the online peak wavelength to the first offline peak wavelength for the surface, and $E_{Offx}$ is the scaled received pulse energy of the first or second offline laser beam.

* * * * *